United States Patent
Szymanski et al.

(10) Patent No.: US 6,831,037 B2
(45) Date of Patent: Dec. 14, 2004

(54) CATALYST CARRIERS

(75) Inventors: Thomas Szymanski, Hudson, OH (US); Donald J. Remus, Stow, OH (US); John R. Lockemeyer, Sugar Land, TX (US); Randall Clayton Yeates, Sugar Land, TX (US); William H. Gerdes, Hudson, OH (US)

(73) Assignee: Saint-Gobain Norpro Corporation, Stow, OH (US)

( * ) Notice: Subject to any disclaimer, the term of this patent is extended or adjusted under 35 U.S.C. 154(b) by 354 days.

(21) Appl. No.: 10/082,761

(22) Filed: Feb. 25, 2002

(65) Prior Publication Data
US 2003/0162655 A1 Aug. 28, 2003

(51) Int. Cl.$^7$ ................................................. B01J 23/00
(52) U.S. Cl. .................. 502/355; 502/263; 502/346
(58) Field of Search .............................. 502/355, 346, 502/243, 263

(56) References Cited

U.S. PATENT DOCUMENTS

| | | |
|---|---|---|
| 2,069,060 A | 1/1937 | Fessler |
| 4,761,394 A | 8/1988 | Lauritzen |
| 4,812,437 A | 3/1989 | Nojiri et al. |
| 4,822,900 A | 4/1989 | Hayden |
| 4,845,296 A | 7/1989 | Ahmed et al. |
| 4,908,343 A | 3/1990 | Bhasin |
| 4,939,114 A | 7/1990 | Nojiri et al. |
| 5,057,481 A | 10/1991 | Bhasin |
| 5,063,195 A | 11/1991 | Jin et al. |
| 5,100,859 A | 3/1992 | Gerdes et al. |
| 5,145,824 A | 9/1992 | Buffum et al. |
| 5,187,140 A | 2/1993 | Thorsteinson et al. |
| 5,380,697 A | 1/1995 | Matusz et al. |
| 5,384,302 A | 1/1995 | Gerdes et al. |
| 5,395,812 A | 3/1995 | Nagase et al. |
| 5,512,530 A | 4/1996 | Gerdes et al. |
| 5,733,842 A | 3/1998 | Gerdes et al. |
| 5,739,075 A | 4/1998 | Matusz |
| 5,929,259 A | 7/1999 | Lockemeyer |
| 6,103,916 A | 8/2000 | Takada et al. |
| 6,114,553 A | 9/2000 | Kiriki et al. |

FOREIGN PATENT DOCUMENTS

| | | |
|---|---|---|
| EP | 003642 | 8/1979 |
| EP | 076504 | 4/1983 |
| EP | 266015 | 5/1988 |
| EP | 0 327 356 | 2/1989 |
| EP | 0 480 538 B1 | 10/1991 |
| EP | 0 496 386 | 1/1992 |
| EP | 927575 | 7/1999 |
| JP | 11240777 | 9/1999 |
| JP | 2000044331 | 2/2000 |
| WO | WO 97/46317 | 6/1997 |
| WO | WO 00/15333 | 3/2000 |
| WO | WO 00/15334 | 3/2000 |
| WO | WO 00/15335 | 3/2000 |

OTHER PUBLICATIONS

Encycl. of Chemical Technology (Kirk–Othmer) vol. 5, pp 610–633; vol. 9, pp 445–471, no date.
Treatise on Materials Science and Technology Edited by Franklin Wang; vol. 9, pp 79–81, no date.
Introduction to the Principles of Ceramic Processing, (Reed) pp 152–182. © 1988, no month.

Primary Examiner—Stanley S. Silverman
Assistant Examiner—Edward M. Johnson
(74) Attorney, Agent, or Firm—Fay, Sharpe, Fagan, Minnich & McKee, LLP

(57) ABSTRACT

The selectivity and activity of a silver-based olefin epoxidation catalyst is found to be a function of the pore size distribution in the alumina carrier on which it is deposited. Specifically it is found advantageous to provide a carrier which has a minimum of very large pores, (greater than 10 micrometers) and a water absorption of 35 to 55% and a surface area of at least 1.0 $m^2/g$. A method of making such carriers is also described.

11 Claims, No Drawings

CATALYST CARRIERS

BACKGROUND OF THE INVENTION

The present invention relates to ceramic catalyst carriers and particularly to carriers for catalysts useful in the epoxidation of olefins such as for example the oxidation of ethylene to ethylene oxide, ("EO"). For the sake of simplicity the invention will be described in the context of this reaction but it is understood to have wider applicability.

Catalyst performance is assessed on the basis of selectivity and reactor temperature. The selectivity is the percentage of the olefin in the feed stream converted to the desired product under standard flow conditions aimed at converting a fixed percentage of the olefin in the feed stream and in the commercial production of ethylene oxide this figure is usually in the 80's. The percentage of olefin reacted normally decreases with time and to maintain the constant level the temperature of the reaction is increased. However this adversely affects the selectivity of the conversion to the desired product. In addition, the equipment used can tolerate temperatures only up to a certain level so that it is necessary to terminate the reaction when the temperature reaches a level inappropriate for the reactor. Thus the longer the selectivity can be maintained at a high level and at an acceptably low temperature, the longer the catalyst/carrier charge can be kept in the reactor and the more product is obtained. Quite modest improvements in the maintenance of selectivity over long periods yields huge dividends in terms of process efficiency.

Epoxidation catalysts usually comprise a silver component, usually with a modifier co-deposited therewith on a ceramic carrier. It has been found that the nature of this carrier exerts a very significant influence of the performance of the catalyst carried thereon but that the reasons for that influence are not completely clear. Carriers are typically formed of a temperature resistant ceramic oxide such as alpha alumina and in general higher purity has been found to correlate with better performance. However it has been found for example that the presence of minor amounts of elemental impurities in the carrier such as alkali metals and some forms of silica can have a beneficial effect.

Intuitively it might also be considered that the higher the surface area of the carrier, the greater the area available for deposition of the catalyst and therefore the more effective the catalyst deposited thereon. This is however found not always to be the case and in modern carrier/catalyst combinations the tendency is to use a carrier with a surface area of less than 1.0 m²/g since these maintain an acceptable activity and selectivity levels while maintaining the necessary crush strength to withstand long term service in a commercial reactor without losing their physical integrity. In addition it has been found that carriers with high surface areas often have high activity but inferior selectivity.

It has now been found however that the picture with respect to carrier surface area is significantly more complicated than was at first appreciated since the nature of the porosity of the carrier has been found to play a most significant role. This discovery is the foundation for the present invention which has led to the development of a catalyst/carrier combination with excellent activity and unusually prolonged retention of a very high selectivity level at modest temperatures.

SUMMARY OF THE INVENTION

The present invention provides a carrier for an olefin epoxidation catalyst which comprises at least 95% alpha alumina with a surface area of from 1.0 to 2.6 m²/g and preferably at least 1.6 to 2.2 m²/g and a water absorption of from 35 to 55%, wherein the pores are distributed such that at least 70%, and preferably at least 80% of the pore volume is provided by pores that have pore diameters from 0.2 to 10 micrometers and provide a pore volume of at least 0.27 mL/g of the carrier. In preferred carriers according to the invention pores with diameters greater than 10 micrometers represent from 0 to 20% and preferably from 0 to 15% of the total pore volume. More preferably still pores with pore sizes less than 0.2 micrometer represent from 0 to 10% of the total pore volume. The mercury pore volume is typically up to 0.56 mL/g and more commonly from 0.35 to 0.45 mL/g.

"Surface area" as the term is used herein is understood to refer to the surface area as determined by the BET (Brunauer, Emmett and Teller) method as described in Journal of the American Chemical Society 60 (1938) pp309–316. While the surface area correlates with the number and sizes of the pores and hence the pore volume, it should be noted that as a practical matter the carriers need to have a certain minimum crush strength which in turn is related to the thickness of the walls surrounding the pores. Reducing this thickness makes the walls more likely to rupture under normal loading conditions such that there is a practical limitation to the surface area of the commercially interesting carriers, at least as designed for incorporation in catalyst combinations using current technology.

The pore volume and the pore size distribution are measured by a conventional mercury intrusion device in which liquid mercury is forced into the pores of the carrier. Greater pressure is needed to force the mercury into the smaller pores and the measurement of pressure increments corresponds to volume increments in the pores penetrated and hence to the size of the pores in the incremental volume. The pore volume in the following description was determined by mercury intrusion under pressures increased by degrees to a pressure of $3.0 \times 10^8$ Pa using a Micromeritics Autopore 9200 model (130° contact angle and mercury with a surface tension of 0.473 N/m).

While the pore volume of the carriers according to the invention is at least 0.27 mL/g it is preferred that pores that have pore diameters from 0.2 to 10 microns provide a pore volume between 0.30 to 0.56 mL/g to ensure that the carriers have commercially acceptable physical properties.

Water absorption is measured by measuring the weight of water that can be absorbed into the pores of the carrier as a percentage of the total weight of the carrier. As indicated above this can be in the range 35 to 55% but preferred carriers have a water absorption of 38 to 50% and most preferably from 40 to 45%.

The invention also comprises a method of making a carrier for an olefin epoxidation catalyst which comprises forming a mixture comprising:

a) from 50 to 90% by weight of a first particulate alpha alumina having an average particle size ($d_{50}$) of from 10 to 90, preferably from 10 to 60, and most preferably from 20 to 40 micrometers; and b) from 10 to 50% by weight, based on the total alpha alumina weight, of a second particulate alpha alumina having an average particle size ($d_{50}$) of from 2.0 to 6.0 micrometers;

c) from 2 to 5% by weight of an alumina hydrate;

d) from 0.2 to 0.8% of an amorphous silica compound, measured as silica; and e) from 0.05 to 0.3% of an alkali metal compound measured as the alkali metal oxide;

all percentages being based on the total alpha alumina content of the mixture, and then forming the mixture into particles and firing the particles at a temperature of from 1250 to 1470° C. to form the carrier.

The carrier particles can be formed by any convenient conventional means such as by extrusion or molding. Where finer particles are desired these can be obtained for example by a spray drying process.

Where the particles are formed by extrusion it may be desirable to include conventional extrusion aids, optional burnout material and water. The amounts of these components to be used are to some extent interdependent and will depend on a number of factors that relate to the equipment used. However these matters are well within the general knowledge of a man skilled in the art of extruding ceramic materials.

The average particle size, referred to herein as "$d_{50}$", is the value as measured by a Horiba (or similar) particle size analyzer after five minutes of sonification and represents the particle diameter at which there are equal volumes of particles larger and smaller than the stated average particle size.

The method of the invention is well adapted to produce the carriers of the invention in view of the careful matching of particles sizes of the alumina components. Adjustments to the water absorption can be achieved by incorporation of conventional burnout materials which are typically finely divided organic compounds such as granulated polyolefins, particularly polyethylene and polypropylene, and walnut shell flour. However burnout material is used primarily to ensure the preservation of a porous structure during the green, (or unfired), phase in which the mixture may be shaped into particles by molding or extrusion processes. It is totally removed during the firing to produce the finished carrier. In practice the above pore size limitations mean that the carriers according to the invention do not have excessive numbers of large pores, (that is pores larger than about 10 micrometers), and have relatively few pores below 0.2 micrometer than is usually the case.

The carriers of the invention are preferably made with the inclusion of a bond material comprising silica with an alkali metal compound in sufficient amount to substantially prevent the formation of crystalline silica compounds. Typically the bond also contains a hydrated alumina component such as boehmite or gibbsite. The silica component can be a silica sol, a precipitated silica, an amorphous silica or an amorphous alkali metal silicate or aluminosilicate. The alkali metal compound can be for example a salt such as a sodium or potassium salt. A convenient bond material to be incorporated with the alumina particles used to form the carrier is a mixture of boehmite, an ammonia stabilized silica sol and a soluble sodium salt. The same effect can be achieved by incorporation of conventional ceramic bonds formulated to contain aluminosilicates and an alkali metal component. It is further found that the performance of the carrier/catalyst combination is significantly enhanced if the carrier is washed to remove soluble residues before deposition of the catalyst.

DESCRIPTION OF PREFERRED EMBODIMENTS

Alumina based carriers can be made in a number of different ways, each of which may affect the pore size distribution. Generally they are made by firing particulate mineral components at an elevated temperature until the particles sinter together. Porosity can be affected by the size of the particles sintered together as well as the time of sintering. In a preferred embodiment of the present invention alumina particles with two different median particle size distributions are used: large particles and small particles. These may be added as separate components of the formulation from which the carrier is formed or they may be generated in situ by milling friable agglomerates until the blend of particle sizes obtains has the desired bimodal distribution. Thus, in theory it is also possible to achieve the carriers of the invention by starting with alumina particles with a single distribution mode. It is intended that all such approaches shall fall within the scope of the process claimed herein.

If sintering is continued until the particles are bonded together, either by the formation of bond posts from any added bond material or through sintering, but not to the point at which the porosity resulting from the packing of the particles is significantly reduced, larger particles will result in larger pores and smaller will result in finer pores. As indicated above, water absorption can also be affected by the use of burnout material which allows more complete sintering without too great a reduction in surface area of the carrier.

The use of a bond material reduces the length of sintering time required to bond the particles together and since sintering is commonly associated with reduction in pore volume, the use of such a bond is a feature of this invention. The selection of the bond can also act to produce a more receptive carrier surface. As indicated above, the bond materials include silica in some form together with an alkali metal component which ensures that the silica is in an amorphous form.

The preferred alumina hydrate is boehmite though gibbsite, bayerite or diaspore could also be used. It is also preferred that the carrier be prepared in the form of pellets, the size of which is in general determined by the dimensions of the reactor in which they are to be deposited. Generally however it is found very convenient to use pellets in the form of hollow cylinders with length and cross-sectional dimensions about the same and from 5 to 10 mm. The pellets can be formed from the mixture by any convenient molding process but preferably they are formed by extrusion of the mixture. To facilitate such extrusion the mixture is usually compounded with up to about 25% and preferably from 10 to 20% by weight based on the mixture weight of extrusion aids and burnouts and thereafter enough water is added to make the mixture extrudable. Extrusion aids are well known in the art and include materials such as vaseline, polyolefin oxides and polyethylene glycol. Likewise organic burnouts are well known in the art and include materials such as granulated polyolefins, powdered walnut shells and other fine organic particulates.

The extrusion aids are added in the amounts necessary to facilitate extrusion of the specific formulation and this will be influenced by the particle sizes, amount of bond material, (if any) and water present and the design of the extruder. The actual amount of extrusion aids to be used is not critical to the final product and appropriate amounts will be readily apparent to the man of skill in the art. They are removed completely upon firing. The burnout materials are also added in amounts as desired to cause an increase in the water absorption of the product prepared in accordance with the invention. It is possible that either extrusion aids or burnouts, in appropriate circumstances, could provide the whole of the combined weight of such additives, (as indicated above), that could be added to the formulation.

The shaped pellets are then dried and fired at a temperature high enough to ensure that the alumina particles are joined together by a sintering action or by the formation of bond posts formed from a bond material incorporated in the mixture or by a mixture of the two mechanisms. Generally firing takes place between about 1250 and 1470° C. and preferably about 1300 to 1440° C. for a period of up to about 5 hours and preferably for from 2 to 4 hours.

The effect on pore size distribution of the selection of materials and bonds is illustrated by comparison of the Carriers of the invention, (INV-1, INV-2 and INV-3) with a comparative carrier, (COMP-A). The following Table 1 shows the various significant physical characteristics of the carriers according to the invention and those of Comparative Carrier.

TABLE 1

|  | INV-1 | INV-2 | INV-3 | COMP-A |
|---|---|---|---|---|
| % PORES < 0.2μ | 5 | 9 | 3 | 0 |
| % 0.2–10μ | 92 | 72 | 95 | 64 |
| % > 10μ | 3 | 19 | 2 | 36 |
| Total Hg P.V. mL/g | 0.41 | 0.42 | 0.56 | 0.40 |
| Surface Area m²/g | 2.04 | 2.11 | 2.51 | 0.73 |
| Water Absorption % | 42.4 | 48.9 | 55 | 40.2 |
| 0.2–10μ P.V. mL/g | 0.37 | 0.30 | 0.53 | 0.26 |

P.V. refers to pore volume.

Preparation of Carriers

As indicated above the carriers of the invention can be prepared in a number of ways that would be understood by the man of skill in the art. In the production of a preferred carrier, (INV-1), a mixture was made of the following ingredients, all proportions being by weight as the components exist in the fired carrier:

1. 67.4% of an alpha alumina with an average particle size, (d50), of 29 micrometers;
2. 29% of an alpha alumina with an average particle size, (d50), of 3 micrometers;
3. 3% of boehmite;
4. 0.5% of silica, (in the form of an ammonia stabilized silica sol); and
5. 0.1% of sodium oxide, (in the form of sodium acetate).

The silica and sodium acetate were used together with the boehmite to provide a bond conferring green strength. To this mixture were added 5% by weight of petroleum jelly, 9% of a mixture of fine particulate organic burnouts and 0.1% of the mixture weight of boric acid. Water was then added in an amount to make the mixture extrudable and this mixture was then extruded to form hollow cylinders that are about 8 mm in diameter and 8 mm long. These were then dried and fired in a kiln at 1425° C. to produce the porous alumina carrier of the invention.

The INV-2 carrier was prepared in exactly the same way as INV-1 except that the mixture contained 14% of the mixture of fine particulate organic burnouts rather than 9%. The INV-3 carrier was prepared with 14% of petroleum jelly and 8% fine organic burnouts The COMP-A carrier was made according to the process described in Example 1 of U.S. Pat. No. 5,100,859. The carriers evaluated were all made from aluminas and the proportions and average particle sizes, $d_{50}$, of these components are shown in the following Table 2. The balance of the proportions, to make 100% was bond material.

TABLE 2

| $Al_2O_3$ | COMP-A | INV-1 | INV-2 | INV-3 |
|---|---|---|---|---|
| 1 | 98.8% 3μ | 29% 3μ | 29% 3μ | 20% 3μ |
| 2 |  | 67.4% 29μ | 67.4% 29μ |  |
| 3* |  | 3% | 3% | 3% |
| 4 |  |  |  | 76.4% 16μ |

*indicates boehmite with the amount calculated as $Al_2O_3$

Evaluation of the Carriers

The comparative carrier was then evaluated against the INV.-1 carrier of the present invention. The carriers were used to prepare ethylene oxide catalysts using the method generally described in U.S. Pat. No. 5,380,697. The performance of the carrier according to the invention was then evaluated against the comparative carriers under equivalent conditions.

The catalysts were used to produce ethylene oxide from ethylene and oxygen. To do this, 1.5 to 2 g. of crushed catalyst were loaded into a 6.35 mm. inside diameter stainless steel U-shaped tube. The tube was immersed in a molten metal bath (heat medium) and the ends were connected to a gas flow system. The weight of catalyst used and the inlet gas flow rate were adjusted to give a gas hourly space velocity of 6800 cc/cc of catalyst/hr. The inlet gas pressure was 210 psig.

The gas mixture passed through the catalyst bed, in a "once-through" operation, during the entire test run including the start-up, consisted of 25% ethylene, 7% oxygen, 5% carbon dioxide, 63% nitrogen and 2.0 to 6.0 ppmv ethyl chloride.

The initial reactor temperature was 180° C. and this was ramped up at a rate of 10° C. per hour to 225° C. and then adjusted so as to achieve a constant ethylene oxide content of 1.5 vol % in the outlet gas stream at an ethyl chloride concentration of 2.5 ppmv. Performance data at this conversion level are usually obtained when the catalyst has been on stream for a total of at least 1–2 days.

The initial performance values for selectivity and temperature are reported in Table 3 below.

TABLE 3

| CARRIER | Selectivity (%) | Temperature (° C.) |
|---|---|---|
| INVENTION-1 | 82.5 | 224 |
| INVENTION-2 | 81.9 | 232 |
| COMP-A | 81.9 | 240 |

The catalysts based on the Carrier COMP-A had a selectivity value significantly below that based on the INV-1 carrier and required much higher temperatures. The fact that the reaction maintained the superior selectivity level at such a low temperature, indicated strongly that the formulation based on the Carrier of the invention would have much greater longevity than formulations based on the comparative carrier, (A).

These improvements are highly valuable commercially since the longer the reaction can be run at high levels of activity and selectivity without changing the very expensive catalyst/carrier charge, the more economical is the process.

We claim:

1. A carrier for a catalyst for the epoxidation of an olefin which comprises at least 95% alpha alumina with a surface area of from 1.0 to 2.6 m²/g and a water absorption of from 35 to 55%, wherein the pores are distributed such that at least 70% of the pore volume is in the form of pores having pore diameters from 0.2 to 10 micrometers and pores with diameters between 0.2 and 10 micrometers provide a volume of at least 0.27 mL/g of the carrier.

2. A carrier according to claim 1 in which pores with diameters less than 0.2 micrometers represent from 0 to 10% of the total pore volume.

3. A carrier according to claim 1 in which mercury pore volume is up to 0.56 mL/g.

4. A carrier according to claim 1 wherein the surface area is from 1.6 to 2.2 m$^2$/g.

5. A carrier according to claim 1 wherein the pores are distributed such that pores with pore diameters greater than 10 micrometers represent less than 20% of the total pore volume.

6. A carrier according to claim 1 which further comprises from 0.2 to 0.8% of an amorphous silica compound.

7. A method of making a carrier for an olefin epoxidation catalyst which comprises forming a mixture comprising:
   a) from 50 to 90% by weight of a first particulate alpha alumina having an average particle size ($d_{50}$) of from 10 to 90 micrometers;
   b) from 10 to 50% by weight, based on the total alpha alumina weight, of a second particulate alpha alumina having an average particle size ($d_{50}$) of from 2 to 6 micrometers;
   c) from 2 to 5% by weight of an alumina hydrate;
   d) from 0.2 to 0.8% of an amorphous silica compound, measured as silica; and
   e) from 0.05 to 0.3% of an alkali metal compound measured as the alkali metal oxide;
   all percentages being based on the total alpha alumina content of the mixture, and then forming the mixture into particles and firing the particles at a temperature of from 1250 to 1470° C. to form the carrier.

8. A method according to claim 7 wherein the alumina hydrate is boehmite.

9. A method according to claim 7 wherein the mixture comprises up to 20% by weight of organic burnout material.

10. A method according to claim 7 in which the mixture is compounded with from 10 to 25% based on the mixture weight of extrusion aids and organic burnouts and sufficient water to render the mixture extrudable, and then extruded to form pellets which are then dried and fired to produce the carrier.

11. A method according to claim 7 in which the olefin is ethylene.

* * * * *